US009989065B2

(12) United States Patent
Kamrath

(10) Patent No.: US 9,989,065 B2
(45) Date of Patent: Jun. 5, 2018

(54) CENTRIFUGAL PUMP AND FAN ASSEMBLY

(71) Applicant: Rexair LLC, Troy, MI (US)

(72) Inventor: Robert R. Kamrath, Troy, MI (US)

(73) Assignee: Rexair LLC, Boca Raton, FL (US)

( * ) Notice: Subject to any disclaimer, the term of this patent is extended or adjusted under 35 U.S.C. 154(b) by 81 days.

(21) Appl. No.: 15/169,161

(22) Filed: May 31, 2016

(65) Prior Publication Data

US 2017/0342999 A1    Nov. 30, 2017

(51) Int. Cl.

| B01F 3/04 | (2006.01) |
|---|---|
| F04D 29/08 | (2006.01) |
| F04D 17/16 | (2006.01) |
| F04D 1/00 | (2006.01) |
| F04D 13/14 | (2006.01) |
| F04D 29/28 | (2006.01) |
| F04D 29/22 | (2006.01) |
| F04D 13/16 | (2006.01) |
| F04D 29/42 | (2006.01) |
| A61L 9/12 | (2006.01) |

(52) U.S. Cl.
CPC ............ *F04D 29/083* (2013.01); *A61L 9/122* (2013.01); *B01F 3/04035* (2013.01); *B01F 3/04042* (2013.01); *F04D 1/00* (2013.01); *F04D 13/14* (2013.01); *F04D 13/16* (2013.01); *F04D 17/16* (2013.01); *F04D 29/22* (2013.01); *F04D 29/281* (2013.01); *F04D 29/4226* (2013.01); *A61L 2209/134* (2013.01)

(58) Field of Classification Search
CPC .... B01F 3/04; B01F 3/04007; B01F 3/04021; B01F 3/04035; B01F 3/04042

USPC .................................. 261/83, 84, 85, 88, 91
See application file for complete search history.

(56) References Cited

U.S. PATENT DOCUMENTS

| 2,905,049 A | 9/1959 | Hans | |
|---|---|---|---|
| 3,188,007 A * | 6/1965 | Myklebust | ................ F24F 6/16 239/215 |
| 4,833,895 A | 5/1989 | Johnson | |

(Continued)

FOREIGN PATENT DOCUMENTS

| EP | 2138725 A2 | 12/2009 |
|---|---|---|
| WO | 2012/126052 A1 | 9/2012 |
| WO | 2013/188499 A2 | 12/2013 |

OTHER PUBLICATIONS

International Search Report and Written Opinion, PCT/US2017/034138, 14 pages, Aug. 1, 2017.

*Primary Examiner* — Robert A Hopkins
(74) *Attorney, Agent, or Firm* — Eversheds Sutherland (US) LLP

(57) ABSTRACT

A pump-fan assembly of an air modification device may include a fan, a pump and a disk. The fan may include a central hub disposed on a top surface of the disk, and a plurality of blades extending from the hub towards an outer circumferential edge of the disk. The pump may include a hollow pump body defining an inner tubular passage between an inlet end and a discharge end. An impeller may be arranged at the inlet end and an outlet port may be arranged at the discharge end. The pump and the fan may be coupled at an interface between the discharge end of the pump body and a bottom surface of the disk. The outlet port may be disposed in the interface and arranged to guide a stream of pumped liquid along the bottom surface of the disk. The disk may define a liquid barrier.

18 Claims, 4 Drawing Sheets

(56) References Cited

U.S. PATENT DOCUMENTS

| | | | |
|---|---|---|---|
| 4,840,770 | A | 6/1989 | Walz et al. |
| 5,147,581 | A | 9/1992 | Lu |
| 5,607,627 | A | 3/1997 | Berkeley et al. |
| 6,769,631 | B2 | 8/2004 | Brown |
| 8,770,557 | B2 | 7/2014 | Kanel |
| 8,807,538 | B2 | 8/2014 | Sharma |
| 8,807,540 | B2 | 8/2014 | Sharma et al. |

* cited by examiner

CENTRIFUGAL PUMP AND FAN ASSEMBLY

TECHNICAL FIELD

The present disclosure relates generally to an apparatus for air freshening and/or deodorizing, misting, and the like, and in particular to a centrifugal pump and fan assembly.

BACKGROUND

Various devices and apparatuses have been developed that "freshen" air by delivering a volatizable material such as a fragrance, fragrant, perfume or disinfectant to an environment of use. Such devices, commonly referred to as air fresheners, discharge volatized materials such as fresheners, deodorizers or aromatic vapors into the air to modify the atmosphere of the surrounding environment. Some air freshener devices deliver volatizable material passively or without the need for additional energy input. For example, a passive air freshener may have a reservoir which contains a volatizable material that is released into the environment as the volatizable material evaporates (e.g., ambient evaporation).

In addition to passive devices, active air freshener devices have been developed to aid in the dissemination of the volatizable material. For example, an active air freshener device may have a fan to circulate the volatizable material more rapidly and/or in higher concentration. The fan may be coupled to a power source, such as an electrical motor, to draw in air to enhance the dissemination of the volatizable material from a source such as a reservoir. In this case, a wick or some other type of mechanism is inserted into the reservoir containing the liquid fragrant, where the wick then communicates the volatizable material through its length whereupon the airflow assisted by the fan disseminates the volatizable material.

One type of fan-based air freshener device incorporates a centrifugal fan to assist in circulating the volatizable material such as fragrance laden air and a water reservoir or basin that may contain a fragrance to disperse an aesthetic scent into the environment. Centrifugal fans typically change the direction of airflow after the air enters into the system and expels the air in a radial direction. However, such fan-based devices suffer from various obstacles due at least in part to the centrifugal airflow as well as holes or apertures in the fan that allow the liquid to seep into the exhausted airflow. In particular, air is drawn into the housing and expelled through outlets or vents that are disposed radially from the entry point and/or rotating fan. This forced airflow may induce liquid carry over to the air stream which may cause the device to "weep" or "spit" small drops of liquid out the air vents during operation. Weeping occurs when liquid droplets form within the device near the vents and the rush of forced airflow exhausted therefrom lifts the liquid droplets out of device where they subsequently fall out onto the exterior housing giving an appearance that the housing is weeping. Spitting occurs in a similar manner as weeping and may be described as liquid droplets falling or accumulating on the floor or an area local to the device giving an appearance that the device is spitting out liquid. This "weeping" and/or "spitting" effect may cause damage or even failure to the device, as well as unsightly drawbacks that require cleaning.

Another problem associated with centrifugal fan devices, due at least in part to manufacturing variation in run-out, liquid reservoir over-filling, and/or evaporation or clogging during prolonged use, is the inability to draw a consistent amount of volatizable material such as fragrance containing liquid from the liquid reservoir to disperse the fragrance laden air into the environment.

Accordingly, it has become increasingly desirable to improve the overall design and operation of air freshener devices.

BRIEF DESCRIPTION OF THE DRAWINGS

While the claims are not limited to a specific illustration, an appreciation of the various aspects is best gained through a discussion of various examples thereof. Although the drawings represent illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrates are described in detail by referring to the drawings as follows:

DETAILED DESCRIPTION

Figure 1:
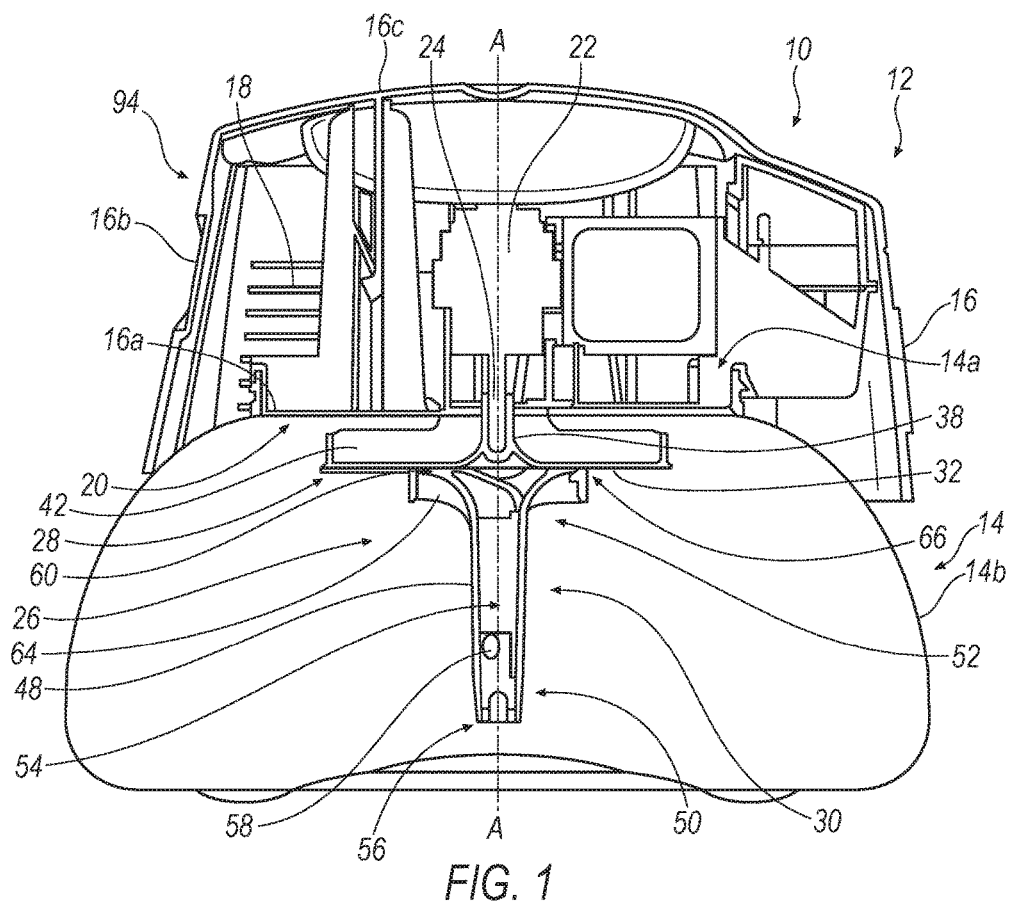
FIG. 1 illustrates a cross-sectional side view of an air modification device.

Referring now to the drawings, exemplary illustrates are shown in detail. The various features of the exemplary approaches illustrated and described with reference to any one of the figures may be combined with features illustrated in one or more other figures, as it will be understood that alternative illustrations that may not be explicitly illustrated or described may be able to be produced. The combinations of features illustrated provide representative approaches for typical applications. However, various combinations and modifications of the features consistent with the teachings of the present disclosure may be desired for particular applications or implementations. The representative illustrations below relate generally to a pump-fan assembly of an air modification device such as an apparatus for air freshening, deodorizing, disinfecting and/or misting. Artisans may recognize similar applications or implementations with other technologies and configurations.

An exemplary pump-fan assembly includes a fan sub-assembly including a disk and a hub disposed on a top or air surface for coupling the fan sub-assembly to a rotating shaft, and a pump sub-assembly coupled to a bottom or liquid surface of the fan sub-assembly in a rotationally secure manner. The pump sub-assembly includes a hollow body extending axially downward into a water basin. The hollow body has a suction end that can be submerged in liquid contained in the basin and a discharge end having one or more outlet ports for dispersing pumped liquid on the bottom side of the disk. Pursuant to certain implementations, the bottom or liquid surface of the fan sub-assembly is sealed throughout a radial extent of the disk to separate a flow of pumped liquid from the top or air surface of the disk. For example, the disk may be configured as a liquid impermeable or impassible barrier to minimize liquid flow, that is, without any holes or apertures that traverse the axial extent or thickness of the disk.

Accordingly, unlike conventional active freshener devices that have at least one aperture or passage in a spinning disk in order to facilitate dispersion of a liquid or a volatized material into the circulating air stream, the pump-fan assembly of the disclosure acts to separate the two moving fluids via a fan disk implemented to minimize or act as a barrier against liquid flow. In one exemplary approach, a liquid impenetrable or impermeable fan disk prevents a significant amount of water from escaping through the air path. Thus, the pump-fan assembly eliminates or at least mitigates the problems associated with weeping and/or spitting.

The pump-fan assembly according to the disclosure is implemented with an intention of producing a consistent amount of liquid, which may be infused with a volatizable material such as a fragrant, to the top of the basin while avoiding the pumped liquid from leaking into the blow air. As the pump-fan assembly is rotated about an axis, the top side of the fan draws in air axially and propels the air radially towards the side of the device housing. At the same time, liquid is propelled up in an axial direction through the pump via an inner tubular passage to the top of the pump, where the liquid is released through outlets and onto a bottom surface of the fan. According to one implementation, the bottom surface of the fan is smooth and non-textured, which allows the pumped liquid to "stick" to the bottom surface of the fan via surface tension. Once the liquid is on the bottom surface of the fan, the liquid flows in streams accelerating radially until the liquid reaches an outer circumferential edge of the fan where the liquid is then flung outwardly spattering onto the inside surface of the basin and falls to the bottom which gives an appearance of a "rain effect" inside of the basin.

By way of the fan disk, the active flow path air and the active flow path of liquid are separated from one another, which reduces or prevents significant amounts of liquid carry over into the air flow path. However, the volatizable material contained in the liquid disperses into the air flow due to a unique flow pattern created by the pump-fan assembly. More specifically, the first active flow path of air interacts with the second active flow path of liquid in a zone disposed radially between the side of the device housing and/or basin and the fan, referred to as a "shear zone." As the air is forced radially outwardly along the top surface of the fan disk and the liquid is accelerated along the bottom surface of the fan disk, the air path and the liquid path flow in adjacent layers or collaterally like two sheets of paper resting against one another, similar to a laminar flow. The air path and the liquid path touch, but do not mix with each other to any significant degree, wherein a certain amount of volatizable material is transferred to the air path and released into the surrounding environment via air vents. The majority of the liquid and volatizable material return to the basin for re-use, which has advantages with respect to reduced consumption of the comparatively expensive volatizable material (e.g., fragrant) as well as extended operating duration between servicing, e.g., until the liquid needs to be replenished.

References made herein to "fragrance," "fragrant," "freshener," "freshening," or other such terms related to exemplary forms of volatizable material should not be interpreted as being limited to deodorizing or pleasing aromas. For example, in some aspects the "fragrance" may be an insect repellant, a disinfectant or antiseptic, an allergen control ingredient or a medicinal substance, while the "freshener" may represent misting of vapors or a form of air circulation without the dispersion of chemicals to mask unpleasant odors. Further, references made herein to "liquid" are intended to encompass unblended liquid, such as water, volatile liquid, such as an oil fragrant, and a mixture or solution of a liquid containing a volatile chemical substance, such as water and fragrant.

Referring now to the Figures, wherein like numerals indicate like or corresponding parts throughout the several views an air modification device is generally shown at 10. As shown in FIG. 1, the air modification device 10 includes a head assembly 12 and a reservoir housing or basin 14 (hereinafter referred to as "basin") for holding a volume of liquid, such as water, and optionally a material such as a fragrant to be volatized, wherein the basin 14 has an opening 14A and is coupled to the head assembly 12 in an assembled state. The basin 14 has a wall or walls 14B that may be composed of a transparent material so as to clearly see the "rain effect" on the inner walls of the basin 14 during operation. The head assembly 12 may include a housing 16 defining an interior and one or more air openings 18 disposed in the housing 16 to facilitate the inflow and outflow of air into the head assembly 12 and one or more air vents 20 for air to enter and exit the basin 14. The head assembly 12 includes a motor 22 disposed within the housing 12, wherein the motor 22 includes an output or drive shaft 24 for rotating about an axis A-A. The drive shaft 24 may extend through a bottom wall 16A of the housing 16 and into an upper portion of the basin 14 via the opening 14A. According to the illustrated example, the housing 16 provides a cover for the basin 14 via the bottom wall 16A and a cap 94 for the motor 22 via a side wall 16B and/or a top wall 16C. The air openings 18 extend circumferentially along the radial side wall(s) 16B of the housing 16 and may comprise louvered openings, although it is contemplated that air openings 18 may be disposed on the axial top wall 16C of the housing 16 or a combination thereof. The air vents 20 are in fluid communication with the basin 14 to facilitate a flow of fluid. According to one implementation, the air vents 20 extend in a circumferential direction around bottom wall 16A the housing 16 and at least partially surround the motor 22 mounted thereon. According to another implementation, the air vents 20 may be configured as an insertable part coupled to the side wall 16B and/or the bottom wall 16A. The bottom wall 16A of the housing 16 may be configured to receive a light for illuminating the basin 14. The head assembly 12 may include one or more switches (not shown) for activating the motor 22 and optionally the light separately or together, and an electrical connection for powering the device 10 if the motor 22 is electrically powered. A pump-fan assembly 26 is arranged at least partially in the basin 14 and drivingly connected to the motor 22 via the drive shaft 24. The pump-fan assembly 26 includes a fan or fan assembly or fan sub-assembly 28 (hereinafter referred to as "fan") for inducing an airflow and a pump or pump assembly or pump sub-assembly 30 (hereinafter referred to as "pump") for drawing in a flow of liquid from the bottom of the basin 14 towards the fan 28. The fan 28 and the pump 30 are arranged coaxially with the rotation axis A-A.

The pump-fan assembly 26 has a rotating disk 32 disposed in a region of the opening 14A of the basin 14 and configured to impede the flow of pumped liquid from entering the airflow. As shown in the example of FIG. 1, the disk 32 is disposed axially below the air vents 20 to facilitate a separation of the airflow and the flow of liquid, although alternate arrangements are contemplated. In the following description, the disk 32 can be used interchangeably as a component of the fan 28 or of the pump 30, and should not be interpreted as limited to a fan disk. As described in greater detail below, the pump-fan assembly 26 delivers a consistent amount of liquid to the top of the basin 14 while preventing the pumped liquid from leaking into the blown air, thereby minimizing or eliminating the "weeping" and "spitting" effect.

Figure 2:
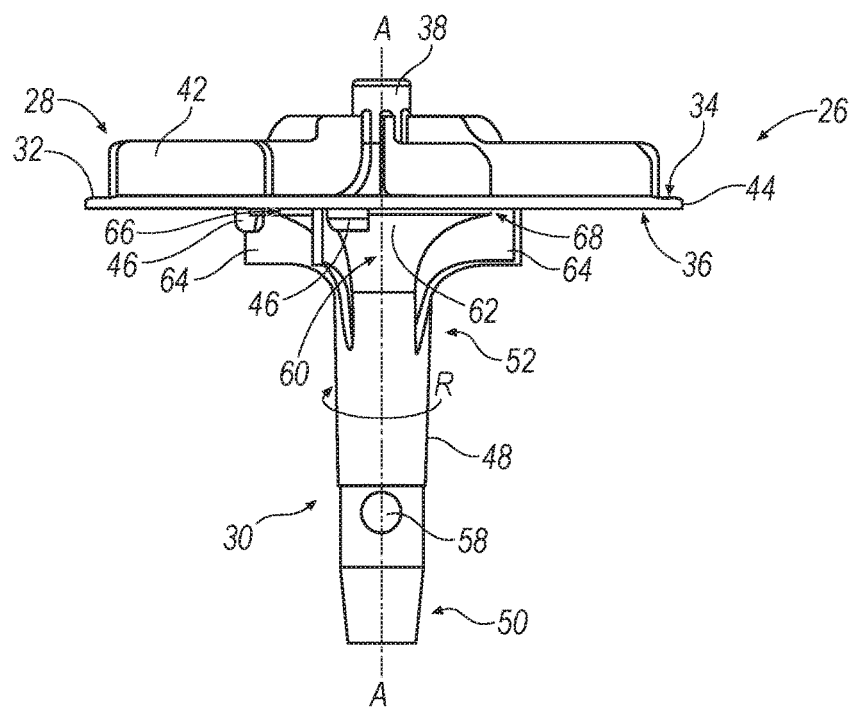
FIG. 2 illustrates a side view of a pump-fan assembly of the air modification device.
Figure 3:
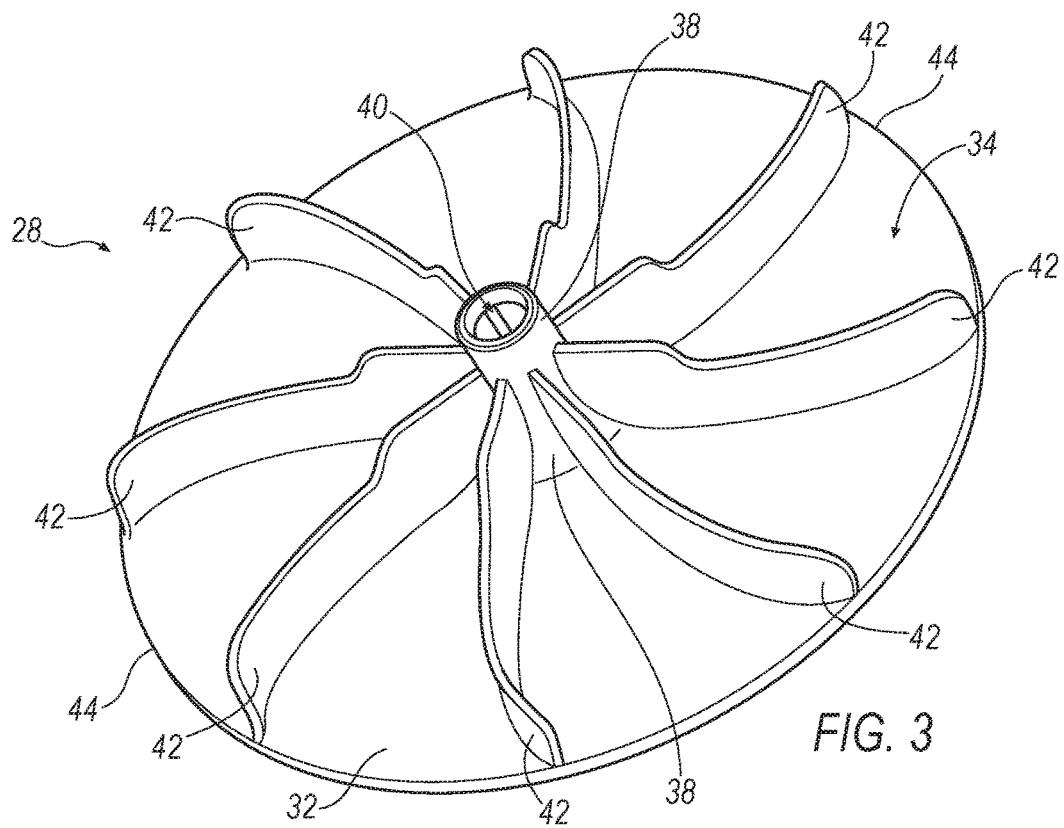
FIG. 3 illustrates an elevated perspective view of a fan for the pump-fan assembly.

Referring to FIGS. 1, 2 and 3, the fan 28 comprises a centrifugal fan that draws in air axially and propels the air out radially. The fan 28 includes a disk 32 having a first, top, air surface 34 and a second, bottom, liquid surface 36. The terms "top" and "bottom" are in relation to the motor 22 and may respectively be identified as an axially upper surface and an axially lower surface in relation to the rotating axis A-A. A central hub 38 is disposed on the top surface 34 of the disk 32 and has a cavity 40 which is press fit onto the drive shaft 24 to connect the pump-fan assembly 26 to the motor 22. Additionally or alternatively, the mating portions of the cavity 40 and the drive shaft 24 may be splined or have a complementary key and keyway to define a spline joint or keyed joint, respectively, to facilitate a secure connection between the rotating drive shaft 24 and disk 32. A plurality of blades 42 are disposed on the top surface 34 and extend from the hub 38 towards an outer periphery or circumferential edge 44 of the disk 32. The plurality of blades 42 may be forward-curved blades, which are curved in a rotating direction R of the fan 28 as they extend from a fixed end adjacent or proximal to an axis of rotation associated with hub 38 radially outwardly to a free end adjacent or proximal to the circumferential edge 44, backward-curved blades, which are curved against the rotating direction R, or straight radial blades. A first connection mechanism 46 is disposed on the bottom surface 36 of the disk 32 for connecting the fan 28 to the pump 30. The first connection mechanism 46 may comprise a plurality of connecting elements including, but not limited to, clips, clasps, hooks, catches or the like.

According to one implementation, the fan 28 may be configured as a one-piece, monolithic and unitary part comprising the disk 32, the hub 38, the blades 42 and the connection mechanism 46. For example, the fan 28 may be formed as a single-unit injection molded part. According to another implementation, the disk 32, the hub 38, the blades 42 and the connection mechanism 46 may each be separate, and when combined together form the fan 28. For example, the hub 38 can be coupled to the disk 32 in a cup-like recess (not shown) via a mechanical and/or material connection. According to another implementation, the hub 38 and the blades 42 may be integrally formed as a single-unit (e.g., an injection molded part) that is coupled to the disk 32. The fan 28 may be composed of a material including plastic, such as polypropylene or some other polymer-based plastic, metal, ceramic, glass, or a combination thereof. As just one non-limiting example, the disk 32 may be formed of plastic and the hub 38 and/or blades 42 may be metal.

According to certain aspects of the disclosure, the fan 28 may define a rigid, impermeable or impenetrable membrane or barrier between the air and the liquid that prevents or at least minimizes the liquid from leaking into the blown air. Pursuant to one implementation, the disk 32 and the hub 38 are formed without holes or apertures throughout its thickness so that the disk 32 extends continuously throughout a radial extent of the bottom surface 36 (e.g., the area defined by the outer circumferential edge 44). That is, the material of the disk 32 and the hub 38 may be formed continuously (e.g., without holes or apertures) so that the pumped liquid cannot leak axially through the fan 28, but rather the pumped liquid is guided along the bottom surface 36 of the disk 32 until the liquid reaches the outer circumferential edge 44 of disk 32 where it is flung off the disk 32. According to another implementation, at least the bottom surface 36 may be sealed throughout a substantial portion or an entire portion of the radial extent of the disk 32 to minimize a liquid flow to the top surface 34. For example, the bottom surface 36 may be formed of a liquid impermeable material such as a continuous sheet, coating or layer of plastic, glass and/or metal. By configuring the fan 28 as a liquid impermeable part, problems with respect to "weeping" and "spitting" are reduced or avoided altogether (at least in any considerable amount). Additionally or alternatively, the top surface 34 and/or the bottom surface 36 may be formed smooth and non-textured which, in the case of the bottom surface 36, facilitates a degree of surface tension to help guide the flowing liquid towards the outer circumferential edge 44.

Consequently, the fan 28 operates in multiple capacities including a centrifugal fan for circulating air, a guide surface for urging the flowing liquid radially outwardly, and an impermeable (liquid) barrier between the blown air and the pumped liquid.

Referring again to FIGS. 1 and 2, the pump 30 includes a hollow body 48 having an inlet or suction end 50 (hereinafter referred to as "inlet end") and a discharge end 52, wherein the body 48 defines an inner tubular flow passage 54 extending axially from the inlet end 50 to the discharge end 52. The pump 30 can be formed of a material similar to that of the fan 28, or the pump 30 and the fan 28 may be formed of different materials. According to an implementation, the pump 30 is formed as a plastic (e.g., polypropylene) injection molded part, although alternative polymer-based plastic, metal and/or ceramic materials are contemplated. Additionally, the pump 30 may include the disk 32 coupled to the body 48, wherein the fan 28 includes the hub 38 and the blades 42 extending from a fixed end adjacent an axis of rotation associated with hub 38 radially outwardly to a free end adjacent the outer circumferential edge 44. In this case, the connection mechanism 46 may be disposed on the hub 38 for connecting with the disk 32.

The body 48 of the pump 30 is conical in shape (e.g., funnel-shaped) and increases in diameter from the inlet end 50 towards the discharge end 52 such that the inner flow passage 54 has a greater diameter at the discharge end 52 than the inlet end 50. An impeller 56 is disposed at the inlet end 50 for axially priming the pump 30, and radial relief ports 58 may be disposed in the body 48 above or downstream the impeller 56 to expel excess priming fluid, wherein two relief ports 58 may be provided that are disposed mutually opposite one another. The impeller 56 may be formed from the same material as the body 48 or from a different material, and may be integral with the body 48 or formed as a separate component coupled to the body 48. A lower portion of the inlet end 50 surrounding the impeller 56 may be tapered to facilitate the flow of liquid on the outside of the body 48 to also move in an upward manner, thereby reducing the likelihood of outside air being sucked into the impeller 56. The discharge end 52 includes a second connection mechanism 60 that interacts with the first connection mechanism 46 disposed on the bottom surface 36 of the disk 32 for coupling the pump 30 to the fan 28. Preferably, the second connection mechanism 60 interacts with the first connection mechanism 46 in such a manner to form a snapped and rotationally fixed connection, and without requiring any attachment or positioning holes formed in the disk 32 and hub 38 of the fan 28 so as to avoid potential leakage of the liquid into the blown air.

The second connection mechanism 60 of the discharge end 52 may comprise a flange 62 flaring outwardly in a radial direction such that the flange 62 defines an outer diameter (or outer periphery) greater than the outer diameter of the inlet end 50 and the discharge end 52. The flange 62 may be integral with the discharge end 52 and thereby define a continuous and indistinguishable extension of the body 48. Although the flange 62 is shown as circular, other non-circular shapes are also contemplated. In the example illustrated in FIGS. 1 and 2, a plurality of detent ribs 64 are arranged on an outer, external surface of the flange 62 that extend from an upper portion of the body 48 up to or past the outer diameter of the flange 62. The detent ribs 64 are configured to engage the first connection mechanism 46 disposed on the bottom surface 36 of the disk 32 to rotationally secure the pump 30 to the fan 28 via a snap-fit connection. The detent ribs 64 advantageously prevent or reduce warping of the body 48, which may cause an increase in pumped liquid run-out variation. Further, the detent ribs 64 may have a curvature similar to that of the fan blades 42 to facilitate a swirling flow of liquid contained in the basin 14 that helps draw liquid into the pump 30. A counter-detent element 84 may be arranged on the flange 62 circumferentially spaced from one or more of the detent ribs 64 to provide a rotational catch on both circumferential sides of the first connection mechanism 46. Thus, the first connection mechanism 46, which may comprise one or more hooks or clasps, are rotationally secured via a snap-fit connection so that the pump 30 can be secured to the fan 28 without any holes or apertures in the disk 32.

At the interface 66 between the discharge end 52 of the pump 30 and the bottom surface 36 of the disk 32, at least one and preferably a plurality of outlet ports 68 are arranged to release the pumped liquid radially so that a plurality of liquid streams are guided along the bottom surface 36 of the disk 32 to the outer circumferential edge 44, where the liquid is then flung out radially by the rotating disk 32 to spatter against an inner wall of the basin 14 and/or an interior of the housing 16.

Figure 4:
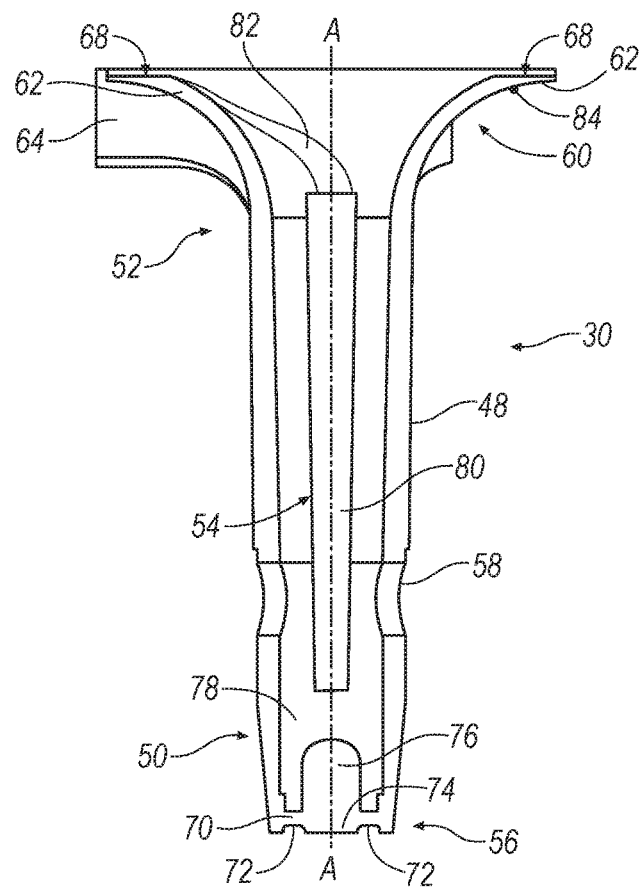
FIG. 4 illustrates a cross-sectional side view of a pump for the pump-fan assembly.
Figure 5:
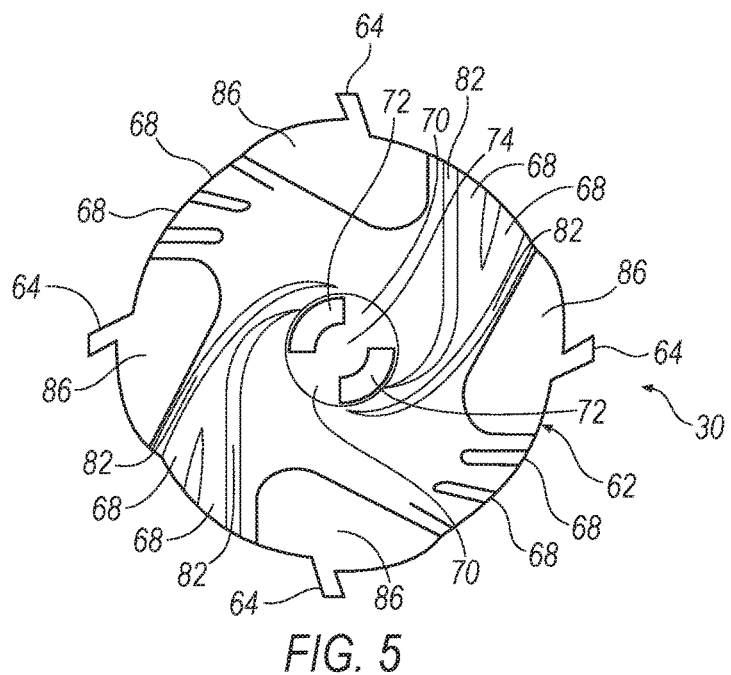
FIG. 5 illustrates a top view of the pump of FIG. 4, according to an implementation.
Figure 6:
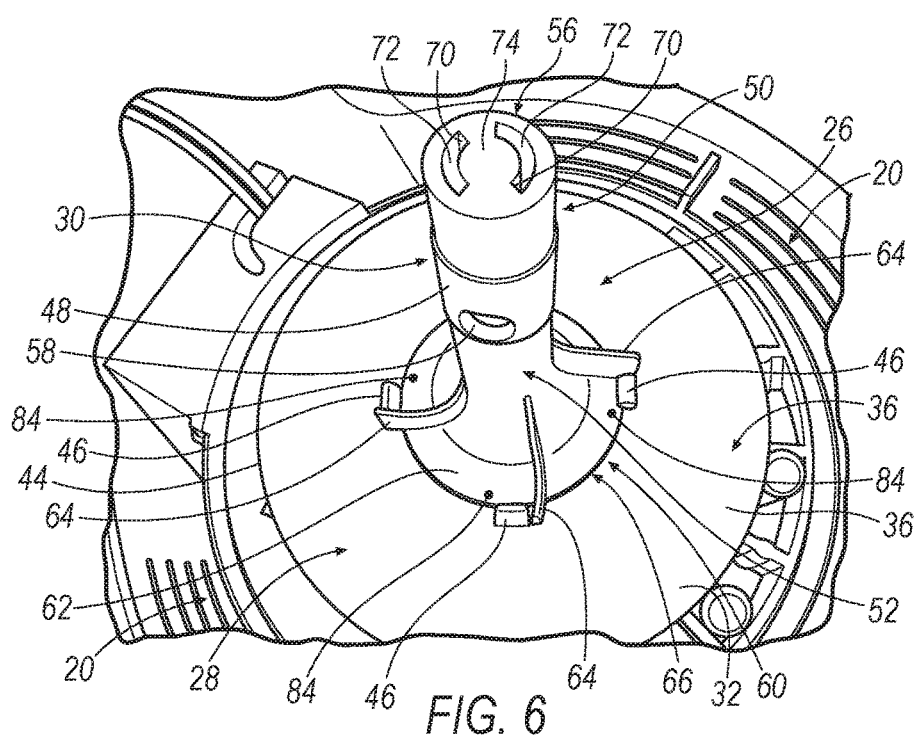
FIG. 6 illustrates a bottom perspective view of the pump-fan assembly mounted to a head assembly of the air modification device of FIG. 1.

As shown in greater detail in FIGS. 4, 5 and 6, the impeller 56 may be disposed within an inner diameter of the inlet end 50 and have one or more impeller blades 70 and one or more inlet openings 72 to force a liquid flow into the body 48, wherein the illustrated example shows two impeller blades 70 and two inlet openings 72 distributed about an impeller eye 74. A bubble plug 76 is disposed in the immediate vicinity of the impeller eye 74 to counteract the submerging of a gas bubble(s) that may form in the inner flow passage 54 at the impeller eye 74, and a capacitance pool 78 may be defined downstream the impeller eye 74 between the bubble plug 76 (or surrounding area) and the relief ports 58 to maintain a sufficient amount of priming liquid.

The body 48 may further include one or more troughs 80 extending in the inner flow passage 54 between the inlet end 50 and the discharge end 52, wherein the illustrated example shows two mutually opposite troughs 80 spaced circumferentially from the relief ports 58. The troughs 80 define a groove in the interior of the body 48 having a geometry, such as a parabolic angle geometry, configured such that the inner flow passage 54 has a greater inner diameter at the troughs 80. Such a configuration of the body 48 via the troughs 80 delivers a small percentage of the fluid in the capacitance pool 78 to the outlet ports 68 above, the remainder of the fluid being exhausted through the relief ports 58. Accordingly, the troughs 80 induce rotational acceleration of the liquid so that a metered amount of liquid is more quickly pushed outwardly by centrifugal force and moves upward along the troughs 80 to the discharge end 52. The troughs 80 may further be configured sloped radially outwards from the rotation axis A-A to centrifugally raise a metered and consistent amount of liquid to the discharge end 52. As shown in the illustrated examples of FIGS. 4 and 5, one or a plurality of channels 82 may extend from an axially top or discharge side of the troughs 80 to the outlet ports 68 to guide the pumped liquid in a consistent manner, wherein the channels 82 may have a curvature similar to that of the fan blades 42 to facilitate a smooth transition of the liquid flow from an axial direction to a radial direction. The size of the outlet ports 68 and the channels 82 controls the size of the water droplets flung out radially from the bottom surface 36 of the disk 32, which influences the extent of the "rain effect" or the spattering of the water droplets against and/or running down the interior of the basin 14.

Referring in particular to FIG. 5, the flange 62 has an inner surface in fluid communication with the flow passage 54 and includes the outlet ports 68 distributed circumferentially about the outer periphery, wherein the channels 82 can be seen extending from the pair of troughs 80 to a corresponding pair of outlet ports 68. The flange 62 in the illustrated example has a tulip-like or trumpeted shape, which serves for improving the flow characteristics of the discharged liquid as the liquid moves from the inner flow passage 54 to the outlet ports 68. The flange 62 may further include mounting surfaces 86 that engage and rest substantially flush with the bottom surface 36 of the fan disk 32. The mounting surfaces 86 may include a greater thickness than the remaining portions of the flange 62 to enhance the snap-fit connection between the pump 30 and the fan 28, which may be snapped into place via a twisting motion. If the flange 62 includes mounting surfaces 86, the outlet ports 68 are distributed circumferentially between adjacent mounting surfaces 86.

The assembled pump-fan assembly 26 is shown in greater detail in FIG. 6, wherein the discharge end 52 of the pump 30 via the flange 62 is coupled to the bottom surface 36 of the fan disk 32. The detent ribs 64 and the counter-detent elements 84 of the flange 62 rest on both circumferential sides of the first connection mechanism 46 of the disk 32, wherein the first connection mechanism 46 has an axial hook or overlap engaging the flange 62, to rotationally, axially and radially secure the pump 30 and the fan 28 to one another. The pump-fan assembly 26 is then coupled to the motor 22 via a press-fit connection between the fan hub 38 and the drive shaft 24, and the head assembly 12 is mounted on the basin 14 to the assembled state as shown in FIG. 1.

Figure 7:
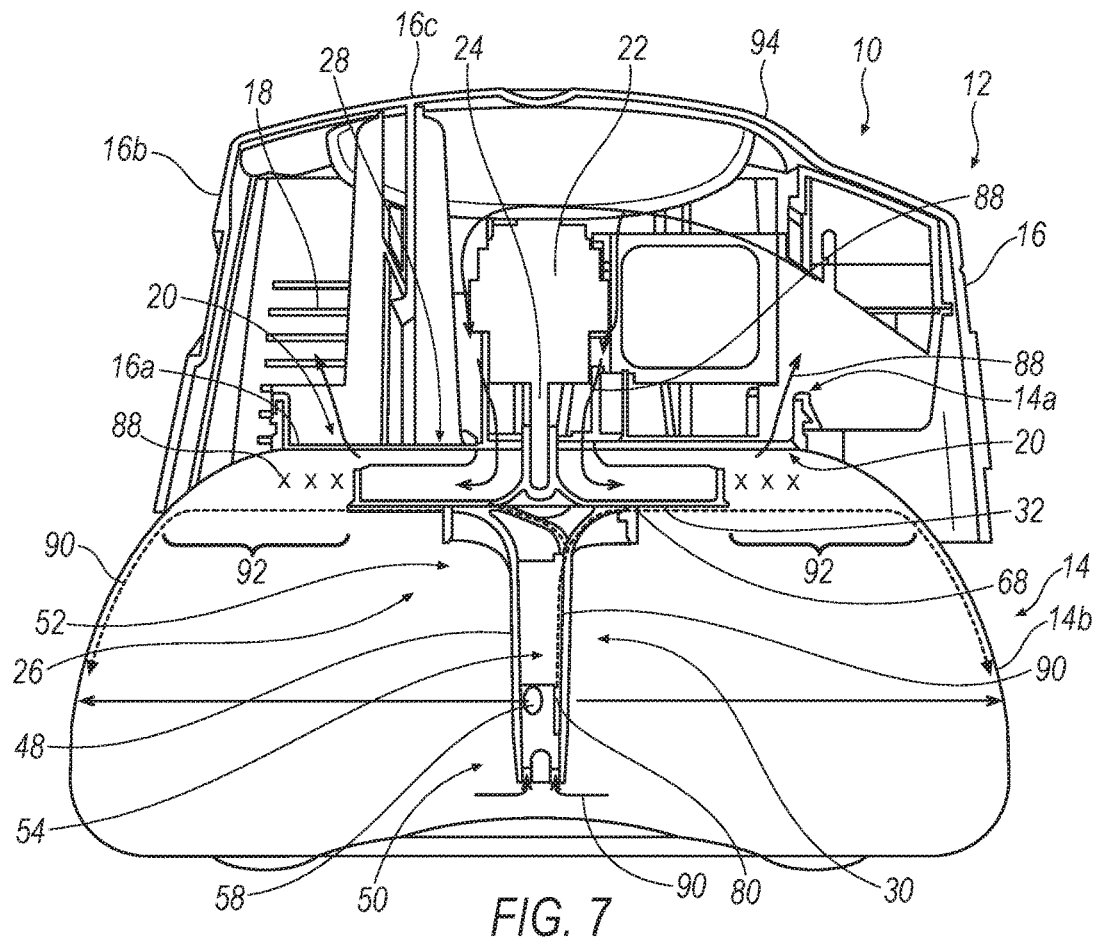
FIG. 7 illustrates a cross-sectional side view of the air modification device of FIG. 1, showing various air and liquid flow paths during operation.

Referring to FIG. 7, the pump-fan assembly 26 produces a unique flow pattern of a liquid flow that is separate from an air flow in the following manner. When the pump-fan assembly 26 is rotated by the motor 22, a first active flow 88 and a second active flow 90 are generated. The first active flow 88 of air enters the cap 94 of the head assembly 12 through the air openings 18 and flows axially into the center of the fan 28 on the top side or side opposite the pump 30. The blades 42 increase the velocity of the air as it moves across the top surface 34 and propels the air radially outwardly into the shear zone 92 between the fan 28 and the interior of the wall(s) 16A, 16B, 16C of the housing 16 and/or the interior of the wall 14B of the basin 14, where the air is then exhaust through the vents 20 at least partially surrounding the opening 14A of the basin 14 and out of the cap 94 of the head assembly 12 via the openings 18. In the second active flow 90, liquid from the basin 14 is forced into the body 48 of the pump 30 by the impeller 56 and the liquid flows up the body 48 via the inner flow passage 54, which axially upward flow is facilitated by the troughs 80 and the increasing diameter of the inner flow passage 54. The pump 30 delivers a metered and intended consistent flow of liquid to the discharge end 52 at least in part due to the troughs 80 and by drawing in a higher volume at the inlet end 50 and expelling excess liquid through the relief ports 58. Once at the discharge end 52, the liquid flow (e.g., liquid droplets) is guided to the bottom surface 36 of the disk 32 via the channels 82 and outlet ports 68, and then moves across the bottom surface 36 of the disk 32 until the liquid reaches the outer circumferential edge 44. Surface tension facilitated by a smooth, non-textured bottom surface 36 aids in the guiding of the liquid radially across the disk 32. The liquid is then flung out radially through the shear zone 92 and spatters against an interior of the wall 14B of the basin 14 and/or an interior of the wall(s) 16A, 16B, 16C of the housing 16 where the liquid returns to the pool at the bottom of the basin 14 via a "rain effect" of liquid falling along the wall 14B of the basin 14.

The disk 32, which also functions as a liquid barrier as discussed above, accelerates the first active flow 88 of air along the top surface 34 and the second active flow 90 of liquid along the bottom surface 36 so that the air path and the liquid path flow into the shear zone 92 collaterally or in substantially adjacent and parallel layers. The air flow and the liquid flow touch one another in the shear zone 92, but do not mix with each other in any significant amount. The pump-fan assembly 26, therefore, has significant improvements with respect to liquid carry over from the second active path 90 of liquid into the first active flow 88 of air that gives rise to the "weeping" and "spitting" effect. In the shear zone 92, fragrance and water vapor are transferred from the second active flow 90 of liquid to the first active flow 88 of air, which then exits into the environment via the vents 20 and openings 18 to freshen, deodorize, and/or mist the atmosphere. The majority or substantial portion of the liquid and fragrant return back to the basin 14 via the "rain effect," which provides savings with respect to liquid and fragrant consumption as well as an aesthetically pleasing look.

It will be appreciated that the aforementioned devices and systems may be modified to have some components removed, or may have additional components added, all of which are deemed to be within the spirit of the present disclosure. Even though the present disclosure has been described in detail with reference to specific examples, it will be appreciated that a plurality of variants and changes can be made to these examples without departing from the scope of the present disclosure as set forth in the claims. It is anticipated and intended that future developments will occur in the technologies discussed herein, and that the disclosed systems and devices will be incorporated into such future embodiments.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary. Additionally, use of adjectives such as first, second, etc. should be read to be interchangeable unless a claim recites an explicit limitation to the contrary.

What is claimed as new and desired to be protected by Letters Patent of the United States is:

1. An assembly, comprising:
   a fan sub-assembly including a disk rotatable about an axis having an air surface and a liquid surface disposed axially opposite the air surface, a central hub disposed on the air surface for receiving a drive member, and a plurality of blades disposed on the air surface extending from the hub towards an outer peripheral edge of the disk, wherein a first connecting mechanism is disposed on the liquid surface of the disk for receiving a pump with a second connection mechanism interacting with the first connection mechanism; and
   a pump sub-assembly including a hollow pump body having an inlet end and a discharge end, the pump body defining an inner tubular passage extending from the inlet end to the discharge end, at least one trough disposed in the inner tubular passage of the pump body and extending axially between the inlet end and the discharge end, and at least one outlet port disposed at the discharge end and arranged to guide the flow of liquid along the liquid surface of the disk, wherein the discharge end of the pump body includes the second connection mechanism,
   wherein the liquid surface is sealed throughout a radial extent of the disk to separate a flow of supplied liquid from the air surface of the disk.

2. The assembly of claim 1, wherein the liquid surface of the disk extends continuously along a radial direction within the outer circumferential edge to define a barrier to minimize liquid flow.

3. The assembly of claim 1, wherein the inner tubular passage includes at least one channel arranged in a region of the discharge end and extending from a discharge side of the at least one trough to the at least one outlet port.

4. The assembly of claim 1, wherein the pump sub-assembly further includes an impeller arranged at the inlet end, and wherein the pump body includes at least one radial relief opening disposed axially between the impeller and the discharge end.

5. The assembly of claim 1, wherein the disk is integral with one of the fan sub-assembly and the pump sub-assembly.

6. An air modification apparatus, comprising:
   a housing having at least one opening for air to traverse;
   a motor disposed in the housing and having a drive shaft for rotating about an axis;
   a basin coupled to the housing for containing a liquid; and
   a pump-fan assembly coupled to the drive shaft and at least partially extending into the basin, wherein the pump-fan assembly includes:
     a fan assembly including a central hub having a cavity receiving the drive shaft, and a plurality of blades extending outwardly from the hub;
     a pump assembly including a hollow pump body extending into the basin, the pump body having an inlet end, an axially opposite discharge end, and an inner tubular passage extending from the inlet end to the discharge end, the pump assembly further including an impeller arranged at the inlet end, an outwardly flared flange extending from the discharge end, and a plurality of circumferentially distributed outlet ports disposed in an inner surface of the flange;

a disk arranged between the hub of the fan assembly and the pump body of the pump assembly, the disk having a top surface coupled to the hub of the fan assembly and an axially opposite bottom surface;

wherein the pump assembly is rotationally fixed to the fan assembly via a mechanical connection between the flange of the discharge end and the bottom surface of the disk; and wherein the disk defines a liquid barrier throughout a radial extent of the bottom surface.

7. The apparatus of claim 6, wherein in response to the drive shaft rotating about the axis, the fan assembly induces a centrifugal air flow propelled radially along the top surface of the disk and the pump produces a centrifugal liquid flow from the inlet end to the plurality of outlet ports so that the liquid flow is released along the bottom surface of the disk without passing axially through the disk to the top surface.

8. The apparatus of claim 6, wherein at least one of:
the pump body includes at least two mutually opposite troughs extending in the inner tubular passage between the inlet end and the discharge end; and
the pump body includes at least two mutually opposite relief ports disposed proximal to the inlet end.

9. The apparatus of claim 8, wherein the pump body further includes at least two channels extending from the at least two troughs to the plurality of outlet ports.

10. The apparatus of claim 6, wherein the disk is integral with one of the fan assembly and the pump assembly.

11. The apparatus of claim 6, wherein the pump assembly further includes a plurality of detent ribs distributed circumferentially from one another on an outer surface of the flange, and wherein the plurality of detent ribs interact with a connection mechanism disposed on the bottom surface of the disk to define the mechanical connection.

12. The apparatus of claim 6, wherein the inner surface of the flange has a plurality of mounting surfaces for engaging the bottom surface of the disk, and wherein the plurality of mounting surfaces are spaced circumferentially apart from one another.

13. The apparatus of claim 6, wherein the bottom surface of the disk is sealed continuously throughout the radial extent.

14. An assembly, comprising:
a fan sub-assembly including a disk rotatable about an axis having an air surface and a liquid surface disposed axially opposite the air surface, a central hub disposed on the air surface for receiving a drive member, and a plurality of blades disposed on the air surface extending from the hub towards an outer peripheral edge of the disk, wherein a first connecting mechanism is disposed on the liquid surface of the disk for receiving a pump with a second connection mechanism interacting with the first connection mechanism; and a pump sub-assembly including a hollow pump body having an inlet end and a discharge end, the pump body defining an inner tubular passage extending from the inlet end to the discharge end, and at least one outlet port disposed at the discharge end and arranged to guide the flow of liquid along the liquid surface of the disk, wherein the discharge end of the pump body includes the second connection mechanism and a flange having an inner surface mounted to the liquid surface of the disk, and wherein the at least one outlet port is arranged on the inner surface of the flange, wherein the liquid surface is sealed throughout a radial extent of the disk to separate a flow of supplied liquid from the air surface of the disk.

15. The assembly of claim 14, further comprising a plurality of ribs distributed circumferentially on an outer surface of the pump body and extending along the flange towards the disk, wherein the plurality of ribs engage the first connection mechanism of the disk in a rotationally fixed manner.

16. The assembly of claim 14, wherein the liquid surface of the disk extends continuously along a radial direction within the outer circumferential edge to define a barrier to minimize liquid flow.

17. The assembly of claim 14, wherein the disk is integral with one of the fan sub-assembly and the pump sub-assembly.

18. The assembly of claim 14, wherein the pump sub-assembly further includes an impeller arranged at the inlet end, and wherein the pump body includes at least one radial relief opening disposed axially between the impeller and the discharge end.

* * * * *